(12) United States Patent
Tsao et al.

(10) Patent No.: US 7,501,063 B2
(45) Date of Patent: Mar. 10, 2009

(54) APPARATUS FOR COLLECTING NANOPARTICLES

(76) Inventors: Tsung-Ming Tsao, No. 1, Sec 4, Roosevelt Rd., Taipei (TW); Ming-Kuang Wang, No. 1, Sec 4, Roosevelt Rd., Taipei (TW); Pan-Ming Huang, No. 1, Sec 4, Roosevelt Rd., Taipei (TW)

( * ) Notice: Subject to any disclaimer, the term of this patent is extended or adjusted under 35 U.S.C. 154(b) by 467 days.

(21) Appl. No.: 11/322,278

(22) Filed: Jan. 3, 2006

(65) Prior Publication Data

US 2006/0149215 A1 Jul. 6, 2006

(30) Foreign Application Priority Data

Jan. 5, 2005 (TW) .............................. 94100200 A

(51) Int. Cl.
*B01D 61/00* (2006.01)
*C02F 1/44* (2006.01)
*B67D 5/58* (2006.01)

(52) U.S. Cl. ...................... 210/651; 210/649; 210/650; 222/189.06

(58) Field of Classification Search .................. 600/573; 604/500; 977/900; 210/650, 651, 652, 653, 210/654, 655; 436/177, 178
See application file for complete search history.

(56) References Cited

U.S. PATENT DOCUMENTS

| | | | | |
|---|---|---|---|---|
| 4,437,859 A | * | 3/1984 | Whitehouse et al. | 604/131 |
| 4,513,607 A | * | 4/1985 | Coupal | 73/61.63 |
| 5,190,666 A | * | 3/1993 | Bisconte | 210/744 |
| 5,567,619 A | * | 10/1996 | Stone | 436/77 |
| 5,976,824 A | * | 11/1999 | Gordon | 435/29 |
| 2003/0047816 A1 | * | 3/2003 | Dutta | 257/788 |

* cited by examiner

*Primary Examiner*—Max Hindenburg
*Assistant Examiner*—Adam J Eiseman
(74) *Attorney, Agent, or Firm*—Muncy, Geissler, Olds & Lowe, PLLC

(57) ABSTRACT

A collecting apparatus includes a syringe device, a filtering device and a power system. The syringe device contains a sample, and the sample has a plurality of nanoparticles mixed with fluids. The filtering device is connected to the syringe device for collecting the nanoparticles. The power system is coupled with the syringe device for pushing the sample into the filtering device to filter out the nanoparticles.

5 Claims, 6 Drawing Sheets

APPARATUS FOR COLLECTING NANOPARTICLES

RELATED APPLICATIONS

The present application is based on, and claims priority from, Taiwan application Ser. No. 94100200, filed Jan. 5, 2005, the disclosure of which is hereby incorporated by reference herein in its entirety.

BACKGROUND

1. Field of Invention

The present invention relates to a collecting apparatus. More particularly, the present invention relates to a collecting apparatus with a power system for collecting large quantities of nanoparticles.

2. Description of Related Art

For the past two decades, nanotechnology research has brought significant breakthroughs and accumulated abundant observations, especially regarding chemical materials, manufacturing, electronic information, medicine, biochemistry, environmental protection, and power generation.

The invention of the steam engine marked the first industrial revolution; and the inventions of electric power, the electric motor and the internal combustion engine marked the second industrial revolution and transcended the millimeter scale. The invention of the computer based on microelectronic technologies marked the third industrial revolution and began to transcend the micrometer scale. Now, innovative nanotechnology is breaking through the nanoscale barriers and leading the fourth industrial revolution.

Nanotechnology is set to create much new matter, materials and machines for the future. Nanotechnology will thoroughly revolutionize human life over hundreds of years and will specifically make huge improvements to the health, wealth and lives of people.

Therefore, most developed countries have invested much human effort and financial and material resources to actively research the field of nanotechnology. Preparative and collection methods of nanoparticles are key technologies in the field of nanotechnology but are plagued by many obstacles to overcome. Scientists all over the world are presently devoting their efforts to break through these technological problems.

Preparative methods of nanoparticles can be approximately classified into physical and chemical methods whose nanoparticle size must be smaller than 100 nm (where 1 nm=$10^{-9}$ m). How to collect large quantities of nanoparticles in the preparation process is a key problem. Nanoparticles are easily gathered into a big agglutinated body because of their surface activity, and this phenomenon brings great difficulty in collecting them individually. In order to overcome this problem, whether using physical or chemical methods, the nanoparticles are generally allowed to disperse in solution. While sedimenting, large-sized particles first settle to the bottom, leaving nanoscale particles suspended in solution with Brownian movement. Nanoparticles can then be obtained after the water is removed as so-called nanopowder.

Currently, the ultracentrifuge method is mainly used to settle particles. The principle of the ultracentrifuge method is the same as a clothes washing machine, spinning a material to precipitate particles to the bottom according to the centrifugal force and throwing the upper suspensions away to obtain desired particles.

However, finer particles are more difficult to settle, meaning that the fine particles need more time and centrifugal force to become settled. For example, to precipitate nanoparticles of greater than 1 nm diameter within 10 mL of sample, the required centrifuging time is 17.6 hrs at 90,000 rpm (centrifugal force of 470,000×g); to settle nanoparticles of greater than 25 nm diameter, only 119 sec at peak speed is needed.

Although this method can obtain nanoparticles, it consumes much time and cannot collect large quantities of nanoparticles. Thus, this method cannot be employed for industrial mass production.

Filtering using a membrane filter is also used to collect nanoparticles, wherein sample is passed through the membrane filter using hand pressure and drawn into syringe barrel. Membrane filters with pore size of 450 nm are in common use at present, and membrane filters with pore size of under 450 nm are available in 300, 220, 100, 50 and 25 nm sizes according to Millipore, a company specializing in manufacturing membrane filters.

However, the filtering work is harder for smaller pore size, so a pore size of 25 nm is the most difficult to operate. For a 10 mL sample, more than 4 minutes by hand pressure are needed to filter nanoparticles (>25 nm diameter). Moreover, the operator must continue to maintain the pressure by his fingers, so using this filtering method not only is inefficient and collects only low quantities of nanoparticles but also is laborious.

SUMMARY

In view of the foregoing disadvantages inherent in the known methods of collecting nanoparticles, the present invention discloses a hydraulic and automatic operation and a collecting apparatus for highly efficient collection of nanoparticles. In accordance with the present invention, a collecting apparatus and a power system are provided for obtaining nanoparticles in which the collected nanoparticles are essentially captured on the membrane filter within the filtering drive.

In accordance with the foregoing and other aspects of the present invention, a collecting apparatus including at least one syringe device, at least one filtering device and a power system is provided. The syringe device contains a sample, and the sample has a plurality of nanoparticles mixed with fluids. The filtering device is connected to the syringe device for collecting the nanoparticles. The power system is coupled with the syringe device for pushing the sample into the filtering device to filter out the nanoparticles.

The collecting apparatus may also include a plurality of syringe devices. Each of the syringe devices includes a syringe barrel and a plunger assembly. The syringe barrel has a sample receiving space that is variable depending upon the quantity of the sample. The plunger assembly has a plunger rod with a sealing plug at one end which provides a desired engagement between the periphery of the sealing plug and an inner wall of the syringe barrel. The sealing plug periphery sufficiently contacts the inner wall of the syringe barrel to provide a sealing function so that the sample cannot be moved through the sealing plug periphery. The syringe device further has a luer at a sample receiving end of the barrel to which the filtering device can be attached.

The filtering device includes a cone-shaped lid, an O-ring, a membrane filter and a cylindrical holder assembly assembled in order. The O-ring is positioned between the cone-shaped lid and the membrane filter and contacts the membrane filter for providing a substantially fluid-tight seal to prevent leakage of the sample at the filtering device circumference. The cone-shaped lid has a luer on its top connected to the syringe device for passing the sample in a direction past the membrane filter to collect the nanoparticles depending on a hydraulic power. The fluids filtered can be gathered in a collecting bottle.

In order to couple the power system with the syringe device, a framework including a plurality of plates, support springs, tubes and connecting bars may be provided. Each of the plates has holes, and the support springs and tubes may be coupled with the holes and positioned between the plates to maintain heights between the plates. The connecting bars may connect the power system and one of the plates for allowing the plates to move up or down.

The power system includes a cylinder, a control valve, a motor, a pump, a flow valve, a tank and a pressure valve. The power system provides an adjustable hydraulic power to the collecting apparatus in the way of causing the cylinder to raise the syringe device such that the sample is pushed into the filtering device for collecting nanoparticles. When the filtering work is ended, the cylinder can be stopped and then the cylinder is able to be moved to a normal position for the next filtering work.

The characteristics of the present invention are utilization of automatic and hydraulic functions to collect large quantities of nanoparticles (>25 nm diameter) within 24 seconds by using the membrane filter with pore size of 25 nm. For example, a 10 mL sample can be filtered 10 times faster and obtain 30 times the quantity of nanoparticles compared to the prior art methods. The present invention can be applied to a wide range of sciences, including colloid and surface sciences, biochemistry, biotechnology, material sciences, environmental sciences, and medicine.

The present invention can also assist in filtering impurities in aqueous solutions and be used to clean up microorganisms in the air and terrestrial systems. Therefore, the present invention is able to improve environmental quality and be applied to medical hygiene purposes. It has multiple functions, high efficiencies, easy operation, and applicability to a wide range of sciences and technologies.

Additional advantages of the present invention will become readily apparent from the following discussion, particularly when taken together with the accompanying drawings.

BRIEF DESCRIPTION OF THE DRAWINGS

These and other features, aspects, and advantages of the present invention will become better understood with regard to the following description, appended claims, and accompanying drawings where:

DESCRIPTION OF THE PREFERRED EMBODIMENTS

Figure 1:
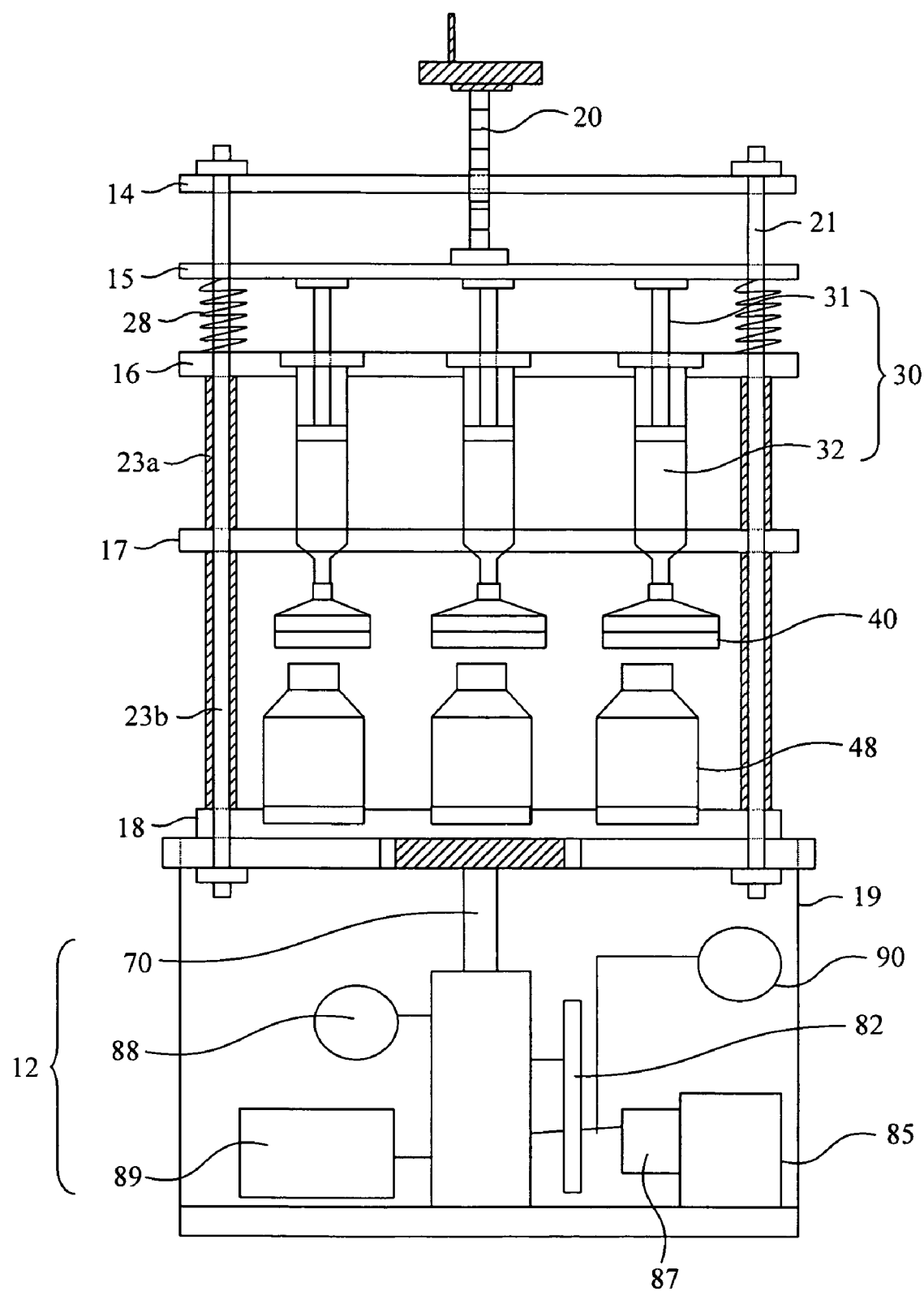
FIG. 1 is an elevation of the collecting apparatus according to one embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Reference is made to FIG. 1, which is an elevation of a collecting apparatus according to one embodiment of the invention. The collecting apparatus includes a plurality of syringe devices 30, a plurality of filtering devices 40 and a power system 12. Each of the syringe devices 30 contains a sample, and the sample has a plurality of nanoparticles mixed with fluids. Each of the filtering devices is connected to one of the syringe devices 30 for collecting the nanoparticles. The power system 12 is coupled with the syringe device 30 for pushing the sample into the filtering device 40 to filter out the nanoparticles.

Figure 2A:
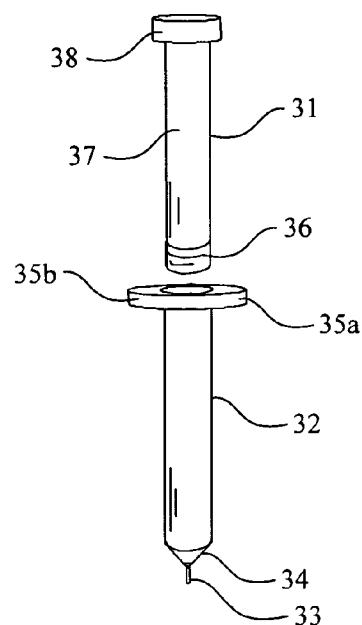
FIG. 2A is an exploded view of one of the syringe devices of FIG. 1.

Reference is made to FIG. 1 and FIG. 2A, which is an exploded view of one of the syringe devices of FIG. 1. Each of the syringe devices 30 includes a syringe barrel 32, which is generally cylindrical in shape along its length, and a sample receiving end 34 of the syringe barrel 32 has a luer 33 to which one of the filtering devices 40 can be attached. Another end opposed to the sample receiving end 34 has a pair of wings 35a, 35b. Moreover, a sample receiving space between both ends can be variable depending upon the quantity of the sample.

Each of the syringe devices 30 further includes a plunger assembly 31. The plunger assembly 31 includes a plunger rod 37 with a disk-shaped member 38 at one end, wherein the plunger assembly 31 and the syringe barrel 32 are able to be moved relatively. The other end of the plunger rod 37 is connected to a sealing plug 36. The sealing plug 36 provides a substantially fluid-tight seal when the sample is positioned in the syringe barrel 32. The sealing plug 36 includes a front face having a sealing periphery. The sealing periphery provides a desired engagement between the sealing periphery and an inner wall of the syringe barrel 32. That is, the sealing periphery sufficiently contacts the inner wall of the syringe barrel 32 to provide a sealing function so that the sample cannot move through the sealing periphery.

Figure 2B:
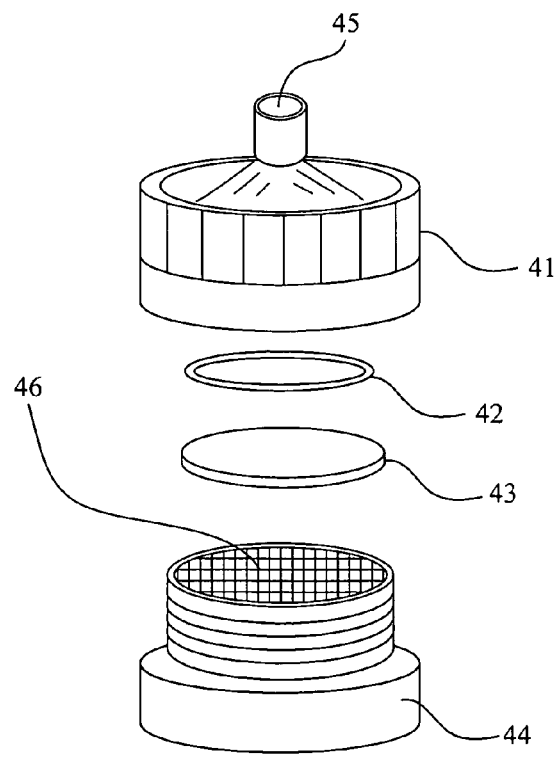
FIG. 2B is an exploded view of one of the filtering devices of FIG. 1.

Reference is made to FIG. 1 and FIG. 2B, which is an exploded view of one of the filtering devices of FIG. 1. The filtering devices 40 are used to filter out the nanoparticles from the syringe devices 30, wherein the sample is pushed into the filtering devices 40 by a hydraulic power. Each of the filtering devices 40 includes a cone-shaped lid 41, an O-ring 42, a membrane filter 43 and a cylindrical holder 44 assembled in order. The cone-shaped lid 41 has a luer 45 on its top to which one of the syringe devices can be attached. The cone-shaped lid 41 further has an inner wall with a threaded hole connected with the cylindrical holder 44. The O-ring 42 provides a substantially fluid-tight seal when the sample is pushed into the filtering devices 40. The cylindrical holder 44 has a cylindrical plane with a metal net 46 for positing the membrane filter 43 on its top, and a path is positioned on the center of the cylindrical plane such that the sample can be pressed along the path through the membrane filter 43 to collect the nanoparticles. The fluids filtered can be gathered in a collecting bottle. The membrane filter 43 is any pore size depending upon the size of the nanoparticles of the sample.

Reference is made to FIG. 1. The collecting apparatus according to one embodiment of the present invention further includes a framework coupling the power system 12 with the syringe devices 30. The framework may include a first plate 14, a second plate 15, a third plate 16, a fourth plate 17 and a fifth plate 18 arranged in a parallel and spaced out relative to each other. Each of the plates is spaced apart in a predetermined height, wherein springs 28 and tubes 23a, 23b are positioned between the plates respectively for maintaining the height. Connecting bars 21 may connect the power system 12 and the first plate 14 through the springs 28 and the tubes 23a, 23b for allowing the plates to move up or down, wherein the inner diameter of the springs 28 and the tubes 23a, 23b is larger than the outer diameter of the connecting bars 21. Both ends of each of the connecting bars 21 further has an outer threaded wall whose diameter is less than the diameter of holes positioned on the first plate 14 for receiving a screw on the upper end of connecting bars 21.

Another end of the connecting bar 21 is inserted through a wall of a power system box 19 and fastened by a nut. The first plate 14 also has a threaded hole on its center, used to couple with a control handle 20 to adjust a first height between the first plate 14 and the second plate 15, such that the disk-shaped member of the plunger assembly 31 may be fixed under the second plate 15. Moreover, the second plate 15 is also used to push the plunger assembly 31 of the syringe devices 30 by the power system 12.

Figure 2C:
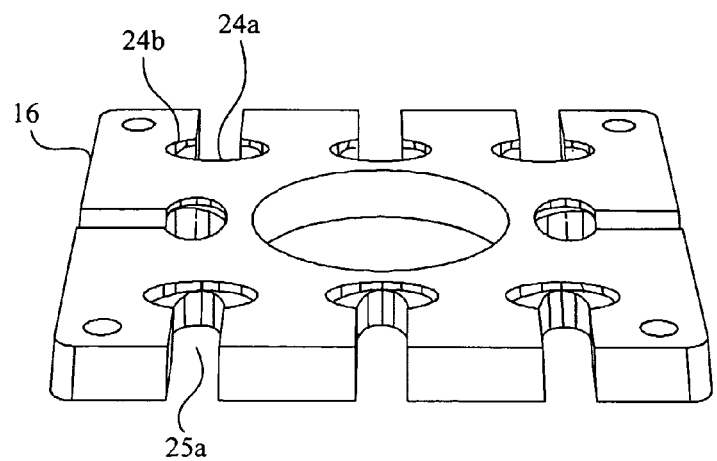
FIG. 2C is a perspective view of the third plate of FIG. 1.

Reference is made to FIG. 1 and FIG. 2C, which is a perspective view of the third plate of FIG. 1. The support springs 28 are positioned between the second plate 15 and the third plate 16 for maintaining a second height between the second plate 15 and the third plate 16 such that the disk-shaped member of the plunger assembly 31 can be fixed under the second plate 15. The third plate 16 has a plurality of gaps 25a on its periphery, wherein the width of the gaps 25a is larger than the diameter of the syringe barrel 32 for allowing the syringe barrel 32 to be assembled and disassembled easily, and thus the wings of the barrel 32 are fixed on recesses 24a and holes 24b of the third plate 16.

Figure 2D:
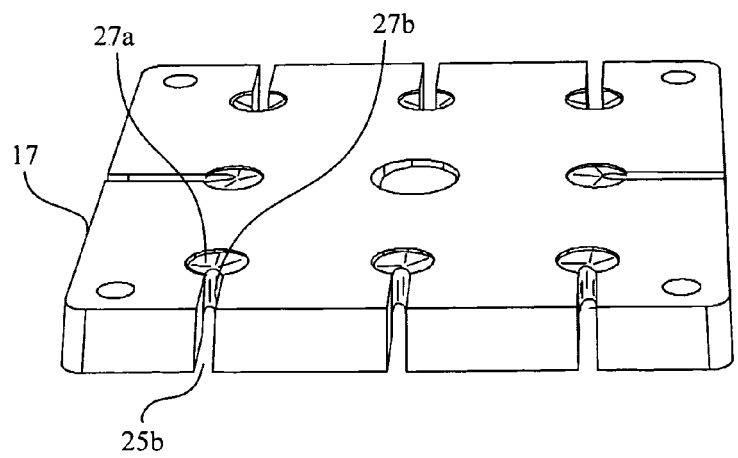
FIG. 2D is a perspective view of the fourth plate of FIG. 1.

Reference is made to FIG. 1 and FIG. 2D, which is a perspective view of the fourth plate of FIG. 1. The support tubes 23a are positioned between the third plate 16 and the fourth plate 17 for maintaining a third height between the third plate 16 and the fourth plate 17, wherein the third height is the same as the length of the syringe barrel 32. In order to fix the sample receiving end and the luer of the barrel 32 on the fourth plate 17, cone-shaped recesses 27a and holes 27b are provided on the fourth plate 17, wherein the size of the cone-shaped recesses 27a and the holes 27b is defined the same as the diameter of the sample receiving end and the luer of the barrel 32 for permitting the sample receiving end and the luer of the syringe barrel 32 to match the cone-shaped recesses 27a and the holes 27b of the fourth plate 17. The fourth plate 17 also includes a plurality of gaps 25b on its periphery, wherein the width of the gaps 25b is larger than the diameter of the luer of the syringe barrel 32 for allowing the barrel 32 to be assembled and disassembled easily.

Figure 2E:
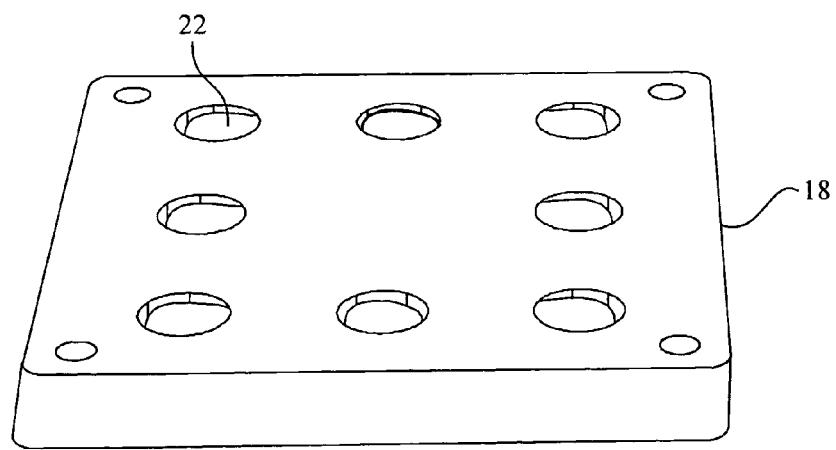
FIG. 2E is a perspective view of the fifth plate of FIG. 1.

Reference is made to FIG. 1 and FIG. 2E, which is a perspective view of the fifth plate of FIG. 1. The support tubes 23b are positioned between the fourth plate 17 and the fifth plate 18 for maintaining a fourth height between the fourth plate 17 and the fifth plate 18, wherein the filtering devices 40 are connected to the luer of the syringe barrel 32 under fourth plate 17. A plurality of collecting bottles 48 are positioned on recesses 22 of the fifth plate 18, wherein the size of the recesses 22 is defined the same as the size of the collecting bottles 48 such that the fluids filtered are gathered in the collecting bottles 48.

Figure 3:
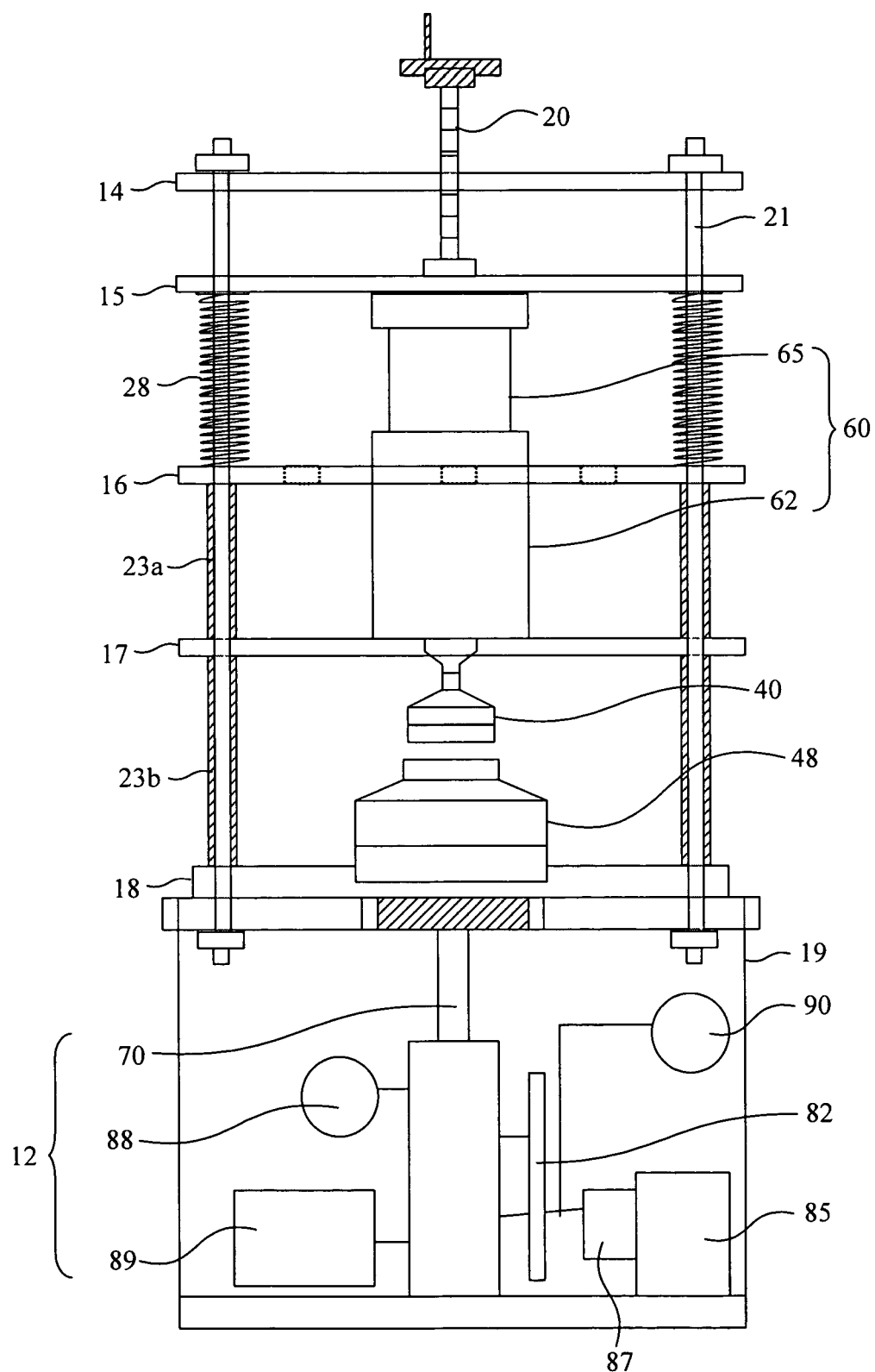
FIG. 3, which is an elevation of the collecting apparatus according to another embodiment of the invention.

Reference is made to FIG. 3, which is an elevation of the collecting apparatus according to another embodiment of the invention. In this embodiment, the syringe devices 30 of FIG. 1 may be changed to a large syringe device 60, depending on the quantity of the sample.

Figure 4:
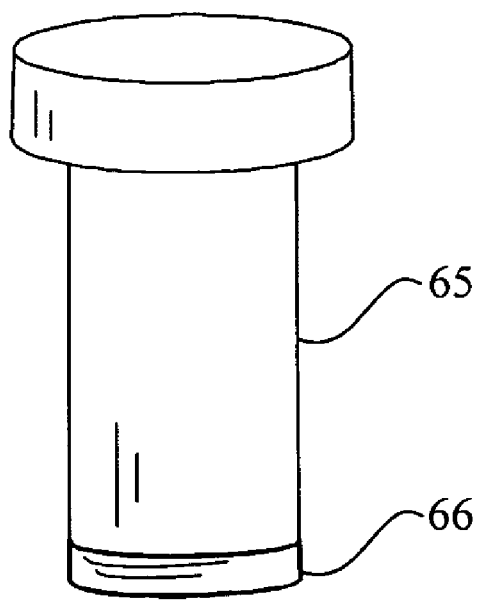
FIG. 4 is an exploded view of the syringe device of FIG. 3.
Figure 4:
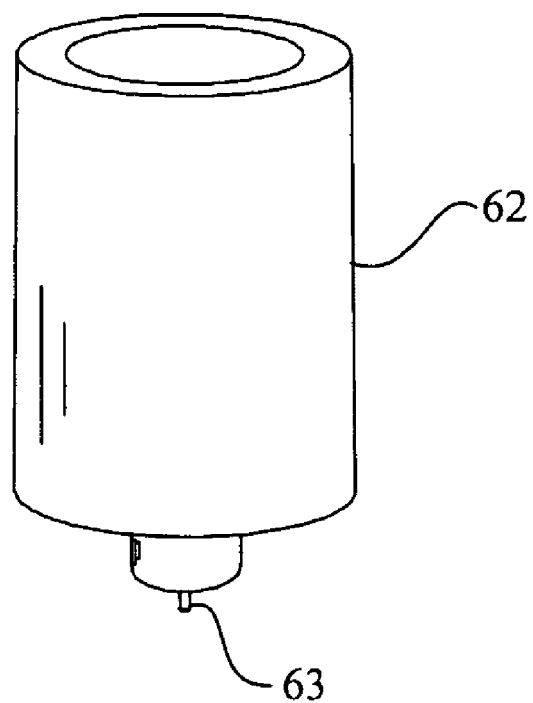

Reference is made to FIG. 3 and FIG. 4, which is an exploded view of the syringe device of FIG. 3. The syringe device 60 includes a syringe barrel 62 with a luer 63 to which a filtering device 40 can be attached. The third plate 16 has a hole coupled with the barrel 62, and the fourth plate 17 also has a hole coupled with the luer 63. The syringe device 60 further includes a plunger rod 65 with a disk-shaped member at one end fixed on the second plate 15, wherein the plunger rod 65 and the barrel 62 can be moved relatively. A sealing plug 66 at another end of the plunger rod 65 includes a front face having a sealing periphery to provide a sealing function so that the sample cannot move through the sealing periphery. The syringe barrel 62 with a large quantity of the sample can be positioned between the third plate 16 and fourth plate 17. The filtering device 40 is connected to the luer 63 of the barrel 62 and the plunger rod 65 is set in the syringe barrel 62. The filtering device 40 can be designed to be adapted for the diameter of the membrane filter, and the membrane filter can also be replaced easily for enhancing the efficiency of the filtering work.

The power system 12 is the main power source during the filtering work. The power system 12 includes a cylinder 70, a control valve 82, a motor 85, a pump 87, a flow valve 88, a tank 89 and a pressure valve 90. The cylinder 70 is coupled with the syringe device 60 and is able to cause the plunger rod 65 and the barrel 62 to be moved relatively.

Figure 5:
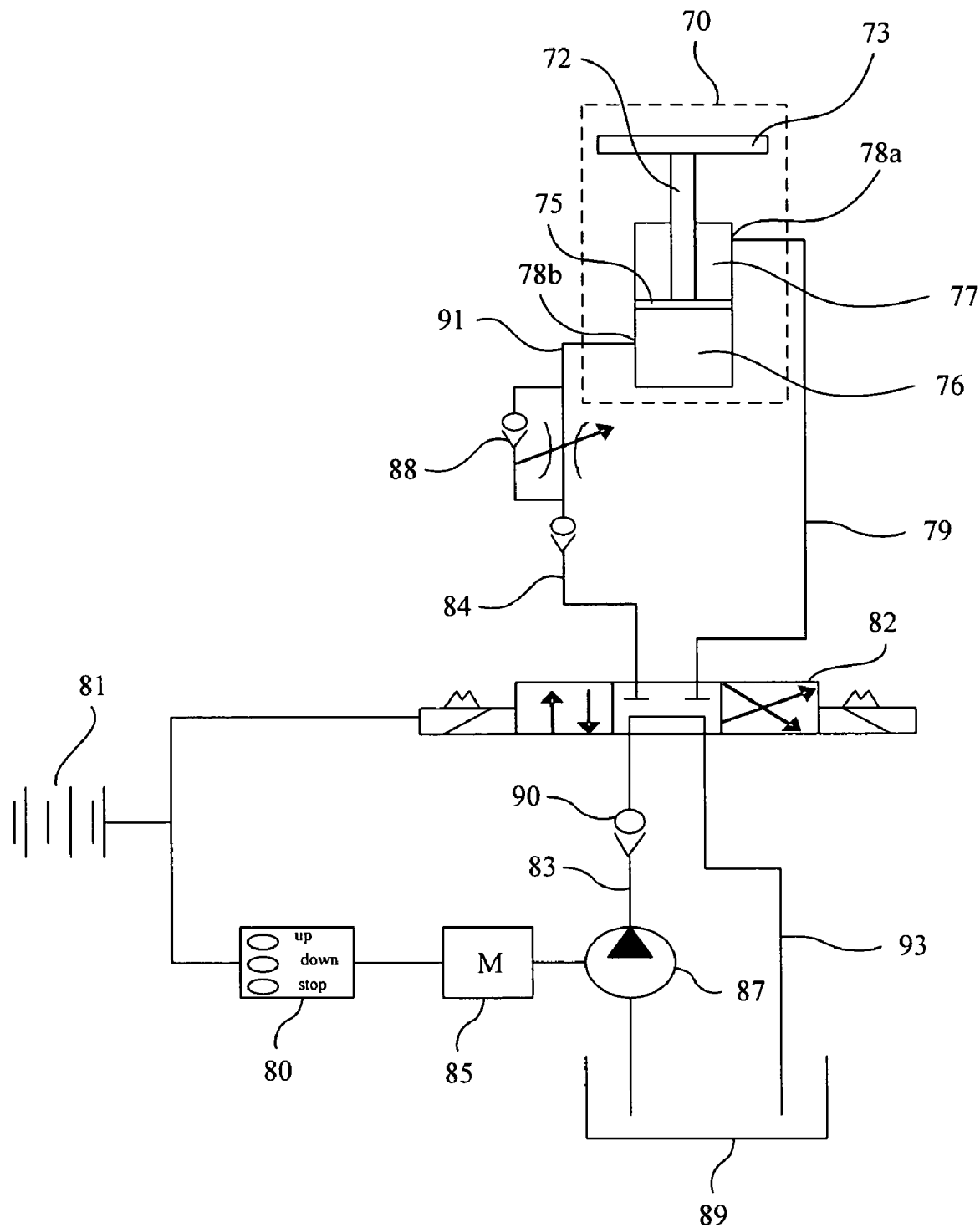
FIG. 5 is a schematic diagram of the power system of FIG. 3.

Reference is made to FIG. 5, which is a schematic diagram of the power system of FIG. 3. The cylinder 70 has a telescoping rod 72. The framework is connected to the upper end 73 of the telescoping rod 72. The cylinder 70 contains a piston 75 which divides the interior of the cylinder 70 into a lower chamber 76 and an upper chamber 77. Both chambers are filled with hydraulic fluids. A lower port 78b is formed on the lower chamber 76, and the lower chamber 76 is injected with hydraulic fluid through the lower port 78b when the piston 75 is moved up. An upper port 78a is formed on the upper chamber 77, and the upper chamber 77 is injected with the hydraulic fluid when the piston 75 is moved down. The flow rate and the pressure of the power system 12 can be controlled by the flow valve 88 and the pressure valve 90. Thus, the piston 75 of the cylinder 70 can be moved at a proper rate.

The power system 12 may further include a three-way electrical switch 80 connected to the control valve 82. The movement of the cylinder 70 can be controlled by the three-way electrical switch 80.

The switch 80 has an up position, a down position and a stop position, used to move up, down and stop the cylinder 70 respectively. In order to move up the cylinder 70, the switch 80 is switched to the up position. Then, the control valve 82 is driven by a power source 81 to conduct the hydraulic fluid from a tube 83 into another tube 84 for injecting the hydraulic fluid into the lower chamber 76. At the same time, the pump 87 and the pressure valve 90 are driven by the motor 85. Thus, the hydraulic fluid is pumped from the tank 89 to the lower chamber 76 of the cylinder 70 through the tube 83, the control valve 82, the tube 84, the flow valve 88 and a tube 91 such that the cylinder 70 is lifted to push the sample into the filtering device. When the cylinder 70 is moved up, the hydraulic fluid originally in the upper chamber 77 may be pushed into the tank 89 through a tube 79, the control valve 82 and another tube 93.

When the switch 80 is switched to the stop position, the control valve 82 is returned to a deactivated state, and the pump 87 and the movement of the cylinder 70 is also stopped.

When the switch 80 is switched to the down position, the control valve 82 is driven by the power source 81 to conduct the hydraulic fluid from the tube 84 into the tube 93. The weight of the framework, the syringe device, the filter device and the collecting bottle causes the hydraulic fluid to be pushed out of the lower chamber 76. The hydraulic fluid is exhausted from the lower chamber 76 of the cylinder 70 into the tank 89 through the tube 84, control valve 82 and the tube 93. Then, the piston 75 can be disposed in its normal adjustment range within the cylinder 70 for the next filtering work.

As mentioned above, it is readily apparent that the structure of the present invention provides an apparatus that employs a power system for collecting nanoparticles automatically at an appropriate operating speed. When users want to collect the nanoparticles, the nanoparticles mixed with fluids are received in a syringe device, and then the nanoparticles are pushed in to a filtering device by the power system. Thus, the nanoparticles are filtered out by the filtering device. Furthermore, when the filtering work is ended, the cylinder of the power system is stopped, and then the cylinder of the power system can be moved to a normal position automatically for the next filtering work.

The foregoing discussion has been presented for purposes of illustration and description. Further, the description does not intend to limit the invention to the form disclosed herein. Variation and modification commensurate with the above teachings, within the skill and knowledge of the relevant art, are within the scope of the present invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A collecting apparatus, comprising:
   at least one syringe device containing a sample, wherein the sample has a plurality of nanoparticles mixed with fluids, wherein the syringe device comprises:
   a syringe barrel having an inner wall, a sample receiving end with a luer, an opposite end having a pair of wings, and a space between the sample receiving end and the opposite end of the syringe barrel for containing the sample;
   a movable rod positioned partially within the syringe barrel; and
   a sealing plug having a front face coupled with the rod for preventing the sample to be moved through the periphery of the sealing plug;
   at least one filtering device connected to the syringe device for collecting the nanoparticles;
   a power system coupled with the syringe device for pushing the sample into the filtering device to filter out the nanoparticles;
   at least one collecting bottle positioned under the filtering device for gathering the fluids; and
   a framework coupling the power system with the syringe device, wherein the framework comprises:
   a first plate having a threaded hole positioned on the center of the first plate;
   a second plate parallel to the first plate;
   a control handle coupled with the threaded hole for maintaining a first height between the first plate and the second plate;
   a third plate parallel to the second plate, wherein the third plate has a syringe hole for fixing the syringe device and a first gap whose width is larger than the diameter of the syringe barrel connecting the syringe hole and the periphery of the third plate;
   at least one support spring positioned between the second plate and the third plate for maintaining a second height between the second plate and the third plate;
   a fourth plate parallel to the third plate, wherein the fourth plate has a cone-shaped hole matching the sample receiving end and the luer of the syringe barrel and a second gap whose width is larger than the diameter of the luer connecting the cone-shaped hole and the periphery of the fourth plate;
   at least one first support tube positioned between the third plate and the fourth plate for maintaining a third height between the third plate and the fourth plate, wherein the third height is the same as the length of the syringe barrel;
   a fifth plate parallel to the fourth plate, wherein the fifth plate has a bottle recess for fixing the collecting bottle;
   at least one second support tube positioned between the fourth plate and the fifth plate for maintaining a fourth height between the fourth plate and the fifth plate; and
   at least one connecting bar connecting the power system and the first plate through the fifth plate, the second support tube, the fourth plate, the first support tube, the third plate, the support spring and the second plate.

2. The collecting apparatus of claim 1, wherein the filtering device comprises:
   a cone-shaped lid connected to the syringe device;
   a cylindrical holder coupled with the cone-shaped lid;
   a membrane filter positioned between the cone-shaped lid and the cylindrical holder, wherein the membrane filter is replaceable; and
   an O-ring positioned between the membrane filter and the cone-shaped lid for providing a substantially fluid-tight seal, wherein the cone-shaped lid having an inner wall with a threaded hole is coupled with the cylindrical holder which has a cylindrical plane with a metal net for positioning the O-ring and the membrane filter on the top of the cylindrical plane.

3. The collecting apparatus of claim 1, wherein the power system comprises: a tank containing hydraulic fluid;
   a cylinder connected to the pump and coupled with the syringe device for pushing the sample into the filtering device to filter out the nanoparticles; and
   a control valve connecting the pump and the cylinder for controlling the movement of the cylinder.

4. The collecting apparatus of claim 3, further comprising a pressure valve connected to the power system such that a pressure of the hydraulic fluid is able to be checked when the pump is pumping.

5. The collecting apparatus of claim 3, further comprising a flow valve connected to the power system such that a push rate of the sample is able to be regulated when the pump is pumping.

* * * * *